(12) United States Patent
Hess et al.

(10) Patent No.: US 7,960,123 B2
(45) Date of Patent: *Jun. 14, 2011

(54) MULTIMARKER PANEL BASED ON PIGF FOR DIABETES TYPES 1 AND 2

(75) Inventors: Georg Hess, Mainz (DE); Andrea Horsch, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 486 days.

This patent is subject to a terminal disclaimer.

(21) Appl. No.: 11/175,933

(22) Filed: Jul. 6, 2005

(65) Prior Publication Data

US 2006/0008829 A1 Jan. 12, 2006

(30) Foreign Application Priority Data

Jul. 7, 2004 (EP) .................................... 04015935

(51) Int. Cl.
*G01N 33/53* (2006.01)
*C07K 14/54* (2006.01)
*C07K 14/58* (2006.01)
*C07K 14/475* (2006.01)

(52) U.S. Cl. ............ 435/7.1; 530/324; 930/50; 930/120; 930/141

(58) Field of Classification Search ........................ None
See application file for complete search history.

(56) References Cited

U.S. PATENT DOCUMENTS 5,744,305 A 4/1998 Fodor et al.

FOREIGN PATENT DOCUMENTS

CA 2509 063 A1 * 6/2005
WO WO 2004046722 A2 * 6/2004

OTHER PUBLICATIONS

Heeschen et al, Jan. 2004. JAMA. 291(4): 435-441.*
Ribatti et al, 2007. Pharmacological Reviews. 59: 185-205).*
Stitt et al, 2005. Diabetes. 54(3): 785-794).*
Cao et al, 1997. Biochemical and Biophysical Research Communications. 235: 493-498.*
Van Regenmortel et al, 1998. Journal of Immunological Methods. 216: 37-48.*
Blann et al, 2002. Clinical Science. 102: 187-194.*
Varo et al. 2003. Circulation. 107: 2664-2669.*
De Lemos et al (2005. Arterioscler Thromb Vasc Biol. 25: 2192-2196).*
Prontera et al (2003. Clinical Chem. 49(9): 1552-1554).*

(Continued)

*Primary Examiner* — Bridget E Bunner
*Assistant Examiner* — Zachary C Howard

(57) ABSTRACT

The present invention relates to a method and means for diagnosing or risk stratification of co-morbidities, particularly cardiovascular complications in diabetes patients. The invention particularly relates to a method for diagnosing whether a diabetes patient is suffering from a cardiovascular complication or is at risk of suffering from a cardiovascular complication, said method comprising the steps of (a) measuring, preferably in vitro, the level(s) of at least one cardiac hormone or a variant thereof in a sample from the patient, and (b) diagnosing the cardiovascular complication or the risk of suffering from cardiovascular complication by comparing the measured level(s) to known level(s) associated with the cardiovascular complication or risk. The present invention also relates to combining the measurement of markers comprising cardiac hormones, natriuretic peptides, inflammation-associated markers, angiogenesis-markers, and markers for platelet activation. Preferred markers are brain natriuretic peptides (particularly NT-proBNP), PlGF, and sCD40L.

4 Claims, 7 Drawing Sheets

OTHER PUBLICATIONS

Koito et al (2004; J. Biochem. 136: 831-837).*
Pepys et al. 2003. J Clin Invest. 111: 1805-1812.*
Luc et al, 2003. Arterioscler Thromb Vasc Biol. 23: 1255-1261.*
Isotani, H. et al., "Plasma Brain Natriuretic Peptide Levels in Normotensive Type 2 Diabetic Pateints without Cardiac Disease," Diabetes Care, vol. 23, No. 5, Jun. 2000, pp. 859-860.
Khaliq, A. et al., "Increased Expression of Placenta Growth Factor in Proliferative Diabetic Retinopathy," Laboratory Investigation, vol. 78, No. 1, pp. 10-116, 1998.
Nielsen, L. et al., "N-terminal pro-brain natriuretic peptide for discriminating between cardiac and non-cardiac dyspnoea," The European Journal of Heart Failure (2003) pp. 1-8.
Siebenhofer, A. et al., "Plasma N-terminal pro-brain natriuretic peptide in Type 1 diabetic patients with and without diabetic nephropathy," Diabetic Medicine, 20, 535-539 (2003).
Yano, Y. et al., "Plasma Brain Natriuretic Peptide Levels in Normotensive Noninsulin-Dependent Diabetic Pateints with Microalbuminuria," The Journal of Clinical Endocrinoloby & Metabolism, vol. 84, No. 7, pp. 2353-2356 (1999).
Beer, S. et al., "Impaired microvascular function is associated with raised plasma N-terminal pro-brain natriuretic peptide level in Type 2 diabetic patients," Diabetologia, vol. 46, No. 2, Aug. 2003.
Cal, J. et al., "Activation of Vascular Endothelial Growth Factor Receptor-1 Sustains Angiogenesis and Bcl-2 Expression Via the Phosphatidylinositol 3-Kinase Pathway in Endohelial Cells," Diabetes, vol. 52, Dec. 2003, p. 2959-2968.
Goede, P. et al., "Multifactorial Intervention an Cardiovascular Disease in Patients with Type 2 Diabetes," The New England Journal of Medicine, vol. 348, No. 5, p. 363-393, Jan. 30, 2003.
Kilhovd, B. at al, "Serum Levels of Advanced Glycation End Products Are Increased in Patients with Type 2 Diabetes and Coronary Heart Disease," Diabetes Care, vol. 22, No. 9, p. 1543-1548, Sep. 1999.
Mitamura, Y. et al., "Vitreous Levels of Placenta Growth Factor and Vascular Endothelial Growth Factor in Patients with Proliferative Diabetic Retinopathy," Diabetes Care, vol. 25, No. 12, Dec. 2002, p. 2352.
Pelsers, M. et al., "Brain-and Heart-Type Fatty Acid-Binding Proteins in the Brain: Tissue Distribution and Clinical Utility," Clinical Chemistry 50: 1568-1575, 2004.
Reddy, D. et al., "Utility of NT-BNP as a screening tool for cardiac dysfunction in patients with long-standing diabetes mellitus," European Journal of Heart Failure Supplements, Elsevier, vol. 3, No. 1, Jun. 2004, p. 24.
Yngen, M. et al., "Enhanced P-selectin expression and increased soluble DC40 Ligand in patients with Type 1 diabetes mellitus and microangiopathy: evidence for platelet hyperactivity and chronic inflammation," Diabetologia (2004) 47:537-540.
Masshoshinkei (Peripheral Nerve), 2000, vol. 11, No. 1, pp. 29-34 (English abstract on p. 34).

* cited by examiner

MULTIMARKER PANEL BASED ON PlGF FOR DIABETES TYPES 1 AND 2

RELATED APPLICATIONS

This application claims priority to European application EP 04015935.2 filed Jul. 7, 2004.

FIELD OF THE INVENTION

The present invention relates to risk stratification of patients suffering from diabetes.

BACKGROUND

Presently, diabetes patients are generally treated as a homogeneous group, only being divided in Type 1 and Type 2 diabetes patients. In fact, diabetes patients constitute a very heterogeneous group. Many patients suffer from co-morbidities such as cardiovascular disease or inflammatory disease. More personalized treatment regimens are needed to accommodate the needs of these patients. However, a prerequisite for personalized treatment is the reliable diagnosis of any co-morbidities or specific or predominant manifestation involved in disease prognosis or indicative of complications coming from a specific disease present in a particular patient.

Current diagnostic tools are insufficient for these purposes. For example, cardiovascular disease is frequently misdiagnosed by general practitioners (Svendstrup Nielsen, L., et al., 2003, "N-terminal pro-brain natriuretic peptide for discriminating between cardiac and non-cardiac dyspnoea", The European Journal of Heart Failure). Therefore, simple and reliable diagnostic tools are needed, in particular for general practitioners and/or physicians specialized in diabetes care.

The use of biochemical or molecular markers for diagnosis is known as such. However, diabetes causes a disturbance of many body functions and, consequently, a disturbance of the levels of potential biochemical or molecular markers. It is not known which marker(s) yield valuable information about the physiological or pathological state of a diabetes patient.

Using immunohistochemistry, Khaliq et al. (1998) described that placental growth factor (PlGF) was observed in superficial retinal vessels in diabetic retinae adjacent to neovascular preretinal membranes. Localization of PlGF was weak or absent in diabetic retinae that showed no evidence of neovascular proliferation (Khaliq, A., Foreman, D., Ahmed, A., Weich, H., et al., 1998, "Increased expression of placenta growth factor in proliferative diabetic retinopathy", Laboratory Investigation, vol. 78(1), pp. 109-116). In the same study, it was described that PlGF was present in diabetic vitreous samples but non-detectable in control samples.

There have been attempts to determine whether brain natriuretic peptide (BNP) can be used as a biochemical marker in diabetes patients. Yano et al. (1999) found that BNP may be a sign for renal complications in Type 2 diabetes patients (Yano Y., Katsuki, A., et al., 1999, "Plasma brain natriuretic peptide levels in normotensive noninsulin-dependent diabetic patients with microalbuminuria", The Journal of Clinical Endocrinology & Metabolism, vol. 84(7), pp. 2353-2356). This finding has been questioned by Isotani et al. (2000) who speculate that increased plasma BNP is rather a sign of cardiac dysfunction (Isotani H., Kameoka K., et al., 2000, "Plasma brain natriuretic peptide levels in normotensive Type 2 diabetic patients without cardiac disease", Diabetes Care, vol. 23(6), pp. 859-860). Siebenhofer, et al. (2002) state that the studies in normotensive Type 2 diabetic patients were inconclusive with respect to elevated BNP levels in patients with microalbuminuria. Siebenhofer et al. (2002) found that NT-proBNP levels are increased in Type 1 diabetic patients with albuminuria. The authors concluded that the role of NT-proBNP in patients with diabetic nephropathy and other co-morbidities was unclear.

Cardiovascular complications are frequently left unnoticed in diabetes patients, as diabetes patients often suffer from neuropathy and a lack of pain sensitivity. For example, diabetes patients may suffer from heart disease without experiencing the hallmark symptom of chest pain.

In addition, some diabetes drugs can have cardiotoxic effects, e.g., by blood volume increase, and should only be administered to patients not suffering from or being at risk of suffering from a cardiovascular complication.

SUMMARY OF THE INVENTION

The present invention relates to a method for diagnosing, in a diabetes patient, a cardiovascular complication or a risk of a cardiovascular complication comprising the steps of measuring in vitro the level of at least one angiogenesis marker or a variant thereof in a sample from the patient and diagnosing the cardiovascular complication or the risk of a cardiovascular complication by comparing the measured level to a known level associated with the cardiovascular complication or the risk.

DETAILED DESCRIPTION OF THE INVENTION

Figure 1:
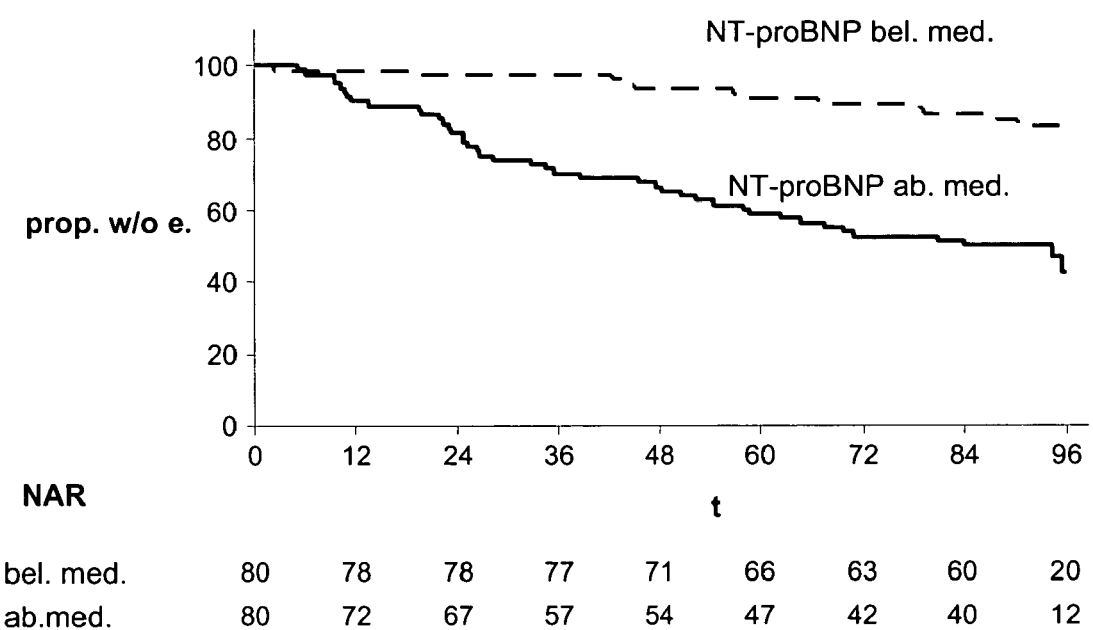
FIG. 1 shows a Kaplan-Meier plot of time to first cardiovascular event in Type 2 diabetic patients with baseline plasma NT-proBNP concentrations below (dashed line) or above the median in the entire cohort. P-value calculated with log-rank test. Prop. w/o e., Proportion without events; t, time (months); NAR, number at risk; bel. med., below median group; ab. med., above median group.

Therefore, it is an object of the present invention to provide methods and means for risk stratification and/or identification of co-morbidities, particularly cardiovascular complications, in patients suffering from diabetes.

In a first embodiment, the problem is solved by a method for diagnosing whether a diabetes patient is suffering from a cardiovascular complication or is at risk of suffering from a cardiovascular complication, comprising the steps of (a) measuring, preferably in vitro, the level(s) of at least one cardiac hormone in a sample from the patient, and (b) diagnosing the cardiovascular complication or the risk of suffering from cardiovascular complication by comparing the measured level(s) to known level(s) associated with the cardiovascular complication or the risk.

The method may also comprise the step of taking a sample, e.g., a body fluid or tissue sample, from the patient. Within the present invention, the taking of the sample can preferably be carried out by non-medical staff, i.e., not having an education necessary for carrying out the profession of a physician. This applies in particular if the sample is blood.

The present invention is particularly advantageous to general practitioners, specialized physicians and wards, departments, or clinics specialized on diabetes treatment, as they frequently have no access to extensive cardiological examination by cardiologists. The present invention provides methods and means to such non-cardiologists for simple and reliable screening of diabetes patients for those patients who are at risk of suffering from a cardiovascular complication.

The present invention provides simple methods and means to detect cardiovascular complications, including heart disease, microangiopathy, platelet activation, and inflammation, in diabetes patients and even in diabetes patients suffering from neuropathy. Detection is possible at early stages of complications, even before irreversible damage has occurred.

The invention takes advantage of certain biochemical or molecular markers. The terms "biochemical marker" and "molecular marker" are known to the person skilled in the art. In particular, biochemical or molecular markers are gene expression products which are differentially expressed, i.e., upregulated or downregulated, in presence or absence of a certain condition, disease, or complication. Usually, a molecular marker is defined as a nucleic acid, such as an mRNA, whereas a biochemical marker is a protein or peptide. The level of a suitable biochemical or molecular marker can indicate the presence or absence of the condition, disease, or complication, and thus allow diagnosis.

Diabetes according to the present invention relates to all forms of diabetes mellitus, including Type 1, Type 2, and gestational diabetes. Particularly, diabetes relates to Type 1 and Type 2 diabetes, most particularly to Type 2 diabetes. Definitions of diabetes mellitus are known to the person skilled in the art, and diagnostic criteria have been established by the World Health Organization (WHO) in 1985 and 1999, as well as by the American Diabetes Association (ADA) in 1997. Any patient fulfilling the criteria according to one or more of these definitions is considered a diabetes patient. Preferably, the diabetes patient is defined according to the WHO 1999 criteria.

Type 1 diabetes is also known as juvenile diabetes or insulin-dependent diabetes mellitus (IDDM). Type 1 diabetes can be caused immunologically (subtype A) and or it can be idiopathic (subtype B). Type 2 diabetes is also known as adult-onset diabetes or non-insulin-dependent diabetes mellitus (NIDDM). Type 2 diabetes can either be accompanied by adipositas (Type 2a) or not accompanied by adipositas (Type 2b). Further types of diabetes are, e.g., caused by genetic defects, diseases of the exocrine pancreas, endocrinopathies, and influences of chemicals or pharmaceutical drugs.

Diagnosing according to the present invention includes determining, monitoring, confirmation, subclassification, and prediction of the relevant disease, complication, or risk. Determining relates to becoming aware of a disease, complication, or risk. Monitoring relates to keeping track of an already diagnosed disease or complication, e.g., to analyze the progression of the disease or the influence of a particular treatment on the progression of disease or complication. Confirmation relates to the strengthening or substantiating of a diagnosis already performed using other indicators or markers. Subclassification relates to further defining a diagnosis according to different subclasses of the diagnosed disease, e.g., defining according to mild and severe forms of the disease. Prediction relates to prognosing a disease or complication before other symptoms or markers have become evident or have become significantly altered.

The term "patient" according to the present invention relates to a healthy individual, an apparently healthy individual, or, particularly, an individual suffering from diabetes. Particularly, the patient is suffering from or being treated for diabetes Type 2 and/or diabetic nephropathy. Even more particularly, the patient has no known history of cardiovascular complication and/or is not being treated for a cardiovascular complication.

The present invention allows diagnosing whether a diabetes patient is suffering from a cardiovascular complication or is at risk of suffering from a cardiovascular complication. "Suffering from a cardiovascular complication" according to the present invention also includes deterioration of a pre-existing cardiovascular complication.

"Cardiovascular complication" can be any cardiovascular disease or event known to the person skilled in the art, including heart disease, microangiopathy, or platelet activation.

The present invention takes advantage of cardiac hormones, angiogenesis markers, and markers for platelet activation as biochemical and molecular markers.

In a first aspect of the present invention, it has been found that cardiac hormones, particularly NT-proBNP, as biochemical or molecular markers are highly indicative of a cardiovascular complication, particularly heart disease, in diabetes patients. It has also been found that markers for microangiopathy are indicative of mortality of cardiovascular disease in diabetes patients.

Therefore, the present invention relates to measuring the level of an angiogenesis marker for diagnosis of a cardiovascular complication or risk of suffering from cardiovascular complication, more particularly microangiopathy.

Thus, the present invention also allows the diagnosis of "microangiopathy". Microangiopathy is a frequent consequence of diabetes and is also known as diabetic microangiopathy. Microangiopathy manifests itself mostly in kidney and retina. Microangiopathy of the kidney can lead to diabetic nephropathy, which is characterized by proteinuria (increased urinary albumin excretion), hypertonia, and progressing kidney insufficiency due to glomerulosclerosis. Microangiopathy of the retina can eventually lead to retinal blood vessel proliferation, retinal bleeds, and blindness. Another consequence of microangiopathy is hypoxia of the extremities (typically known as "diabetic foot") which can lead to gangrene and may require amputation of the extremity.

Therefore, angiogenesis markers also allow diagnosis of diabetic nephropathy, diabetic retinal damage, or hypoxia of extremities.

Preferred angiogenesis markers are PlGF (placental growth factor), VEGF (vascular endothelial growth factor), sFlt1 (soluble fms-like tyrosine kinase 1) and variants thereof. The most preferred angiogenesis marker is PlGF and variants thereof.

The term "variants" in this context relates to peptides which are substantially similar to said peptides. The term "substantially similar" is well understood by the person skilled in the art. In particular, a variant may be an isoform or allele which shows amino acid exchanges compared to the amino acid sequence of the most prevalent peptide isoform in the human population. Preferably, such a substantially similar peptide has a sequence similarity to the most prevalent isoform of the peptide of at least 80%, preferably at least 85%, more preferably at least 90%, most preferably at least 95%. Substantially similar are also proteolytic degradation products which are still recognized by the diagnostic means or by ligands directed against the respective full-length peptide.

Examples of variants are known. For example, variants of NT-proANP and NT-proBNP and methods for their measurement have been described (Ala-Kopsala, M., Magga, J., Peuhkurinen, K. et al., 2004, "Molecular heterogeneity has a major impact on the measurement of circulating N-terminal fragments of A-type and B-type natriuretic peptides", Clinical Chemistry, vol. 50(9), 1576-1588).

The term "variant" in the present context is also meant to relate to splice variants. For example, known splice variants of PlGF are PlGF-1 (149 amino acids), PlGF-2 (170 amino acids) and PlGF-3 (221 amino acids). See, e.g., Cai, J., Ahmad, S., Jiang, W. G., Huang, J., et al., 2003, "Activation of vascular endothelial growth factor receptor-1 sustains angiogenesis and Bcl-2 expression via the phosphatidylinositol 3-kinase pathway in endothelial cells", Diabetes, vol. 52, pp. 2959-2968.

The term "variant" also relates to a post-translationally modified peptide such as glycosylated or phosphorylated peptide. A "variant" is also a peptide which has been modified after collection of the sample, for example, by covalent or non-covalent attachment of a label, particularly a radioactive or fluorescent label, to the peptide.

In another embodiment, the present invention relates to measuring the level of an angiogenesis marker and additionally measuring the level of a cardiac hormone and/or a marker for platelet activation.

In the context of the present invention, it has been found that cardiac hormones, particularly NT-proBNP, as biochemical or molecular markers are highly indicative of a cardiovascular complication, particularly heart disease, in diabetes patients.

Patients suffering from heart disease can be patients suffering from stable angina pectoris (SAP) and individuals with acute coronary syndromes (ACS). ACS patients can show unstable angina pectoris (UAP), or these individuals have already suffered from a myocardial infarction (MI). MI can be an ST-elevated MI or a non-ST-elevated MI. The occurring of an MI can be followed by a left ventricular dysfunction (LVD). Finally, LVD patients undergo congestive heart failure (CHF) with a mortality rate of roughly 15%.

Heart diseases have been classified into a functional classification system according to the New York Heart Association (NYHA). Patients of Class I have no obvious symptoms of heart disease. Physical activity is not limited, and ordinary physical activity does not cause undue fatigue, palpitation, or dyspnea (shortness of breath). Patients of Class II have slight limitation of physical activity. They are comfortable at rest, but ordinary physical activity results in fatigue, palpitation, or dyspnea. Patients of Class III show a marked limitation of physical activity. They are comfortable at rest, but less than ordinary activity causes fatigue, palpitation, or dyspnea. Patients of Class IV are unable to carry out any physical activity without discomfort. They show symptoms of cardiac insufficiency at rest. If any physical activity is undertaken, discomfort is increased.

Accordingly, patients can be divided into individuals showing no clinical symptoms and those with symptoms, e.g., dyspnea.

Another characteristic of heart diseases can be the "left ventricular ejection fraction" (LVEF), which is also known as "ejection fraction". People with a healthy heart usually have an unimpaired LVEF, which is generally described as above 50%. Most people with a systolic heart disease which is symptomatic generally have an LVEF of 40% or less. As a consequence of impaired LVEF, secondary complications can arise, e.g., pulmonary congestion or congested lung.

Heart disease may also be the result of diabetic macroangiopathy. Diabetic macroangiopathy is similar to arteriosclerosis of the non-diabetic patient. However, it is more vigorous, and manifestation is earlier and more frequent. Consequently, "heart disease" according to the present invention also relates to diabetic macroangiopathy.

In the context of the present invention, "heart disease" particularly relates to coronary heart disease, SAP, ACS, UAP, MI, ST-elevated MI, non-ST-elevated MI, LVD, or CHF.

More particularly, "heart disease" relates to ACS, UAP, MI, ST-elevated MI, non-ST-elevated MI, LVD, or CHF.

A heart disease according to the present invention may cause symptoms, particularly symptoms according to NYHA Class II-IV, more particularly according to NYHA Class III-IV.

A heart disease may be associated with an LVEF of 40% or less.

A heart disease may either be "compensated" or "decompensated". Compensated means that the regular oxygen need of the body can still be satisfied, whereas decompensated means that the regular oxygen need of the body is not satisfied anymore.

The cardiac hormones according to the present invention comprise natriuretic peptides and urotensin. Particularly, cardiac hormones according to the present invention are natriuretic peptides. Also taking advantage of combinations of any cardiac hormones or natriuretic peptides as biochemical markers is considered in the context of the present invention.

Natriuretic peptides according to the present invention comprise ANP-type and BNP-type peptides and variants thereof (see, e.g., Bonow, R. O., 1996, "New insights into the cardiac natriuretic peptides", Circulation 93: 1946-1950).

ANP-type peptides comprise pre-proANP, proANP, NT-proANP, and ANP.

BNP-type peptides comprise pre-proBNP, proBNP, NT-proBNP, and BNP.

The term "variants" is to be understood as defined earlier in this specification.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. Therefore, depending on the time-course that is of interest, either measurement of the active or the inactive forms can be advantageous. The most preferred natriuretic peptides according to the present invention are BNP-type peptides and variants thereof, particularly NT-proBNP and variants thereof.

As mentioned above, the present invention relates to measuring the level of an angiogenesis marker and additionally measuring the level of a cardiac hormone and/or a marker for platelet activation.

Thus, the present invention also relates to additionally measuring the level of a marker for platelet activation for diagnosis of a cardiovascular complication, more particularly for diagnosis of platelet activation.

Thus, the present invention also relates to the diagnosis of "platelet activation". According to the present invention, "platelet activation" relates to any thrombotic event, including platelet activation, platelet aggregation, thrombus formation, and thrombus propagation. These biological mechanisms are representative of the risk that a plaque having already become vulnerable will rupture, resulting in reversible vascular occlusion (UAP) or irreversible vascular occlusion (AMI) which may lead to left ventricular dysfunction (LVD), congestive heart failure (CHF), and death.

Therefore, markers for platelet activation also allow diagnosis of platelet aggregation, thrombus formation, thrombus propagation, the risk that a plaque having already become vulnerable will rupture, UAP, and AMI.

Preferred markers for platelet activation are sCD40L (soluble CD40 ligand), vWF (von Willebrand Factor), and variants thereof. The most preferred marker for platelet activation is sCD40L and variants thereof. The term "variants" is to be understood as defined earlier in this specification.

sCD40L (and its variants) can either be "free" or bound to thrombocytes. If sCD40L is measured in blood serum, both free and thrombocyte-bound sCD40L are measured. If sCD40L is measured in blood plasma, only "free" sCD40L is measured. According to the present invention, measuring the level of free sCD40L is preferred.

Preferably, the angiogenesis marker(s) and/or marker(s) for platelet activation are measured in combination with a cardiac hormone. Measuring the different types of markers can help to confirm the diagnosis of a cardiovascular complication and allows subclassification of whether the cardiovascular complication is a heart disease, microangiopathy, or characterized by platelet activation.

Thus, the present invention and its various embodiments allow not only diagnosis of a cardiovascular complication, but also subclassification of whether said cardiovascular complication predominantly relates to heart disease, microangiopathy or platelet activation.

It is known to the person skilled in the art that "heart disease", "microangiopathy", and "platelet activation" are not completely separate disorders, but that they are interrelated. For example, platelet activation may eventually lead to arterial occlusion and heart disease. Therefore, the present invention relates to diagnosing the predominant characteristic and/or the stage or severity of a cardiovascular complication.

The methods of the present invention can also be accompanied by measurement of one or more markers chosen from the group consisting of CRP, hsCRP, IL-6, or respective variants, glucose, HbA1c, $N^\epsilon$-(carboxymethyl)lysine (CML), and AGEs (advanced glycation end products).

CRP (C-reactive protein), hsCRP (high-sensitivity C-reactive protein), IL-6 (interleukin-6), and their respective variants indicate the presence of inflammation in general. Increased levels of these markers in blood serum are also indicative of inflammatory processes in the cardiovascular system. Thus, increased levels of these markers are indicative of the presence or risk of cardiovascular complication. Therefore, measurement of CRP, hsCRP, IL-6, or a respective variant may be used in combination with other markers according to the present invention for diagnosis of cardiovascular complication or risk of suffering from cardiovascular complication.

Increased levels of glucose, HbA1c, AGEs, or CML primarily indicate that the patient requires a better control of the blood sugar level.

Measuring the level of glucose is routinely used to determine the current blood sugar level in a diabetes patient.

Information about the middle or long-term control of blood sugar can be obtained by measurement of HbA1c, CML, or AGEs.

HbA1c is a glycosylated form of hemoglobin. The lower the level of HbA1c, the better the blood sugar level of the diabetes patient is controlled.

The glycoxidation product $N^\epsilon$-(carboxymethyl)lysine (CML) results from long-term incubation of proteins with glucose. Similar to HbA1c, a low level of CML indicates a good control of the blood sugar level in the diabetes patient.

AGEs (advanced glycation end products) also result from long-term incubation of proteins with glucose. Similar to HbA1c and CML, a low level of AGEs indicates a good control of the blood sugar level in the diabetes patient. In addition, it has been suggested that increased levels of AGEs are associated with coronary heart disease in patients with Type 2 diabetes (Kilhovd, B. K., et al., 1999, "Serum levels of advanced glycation end products are increased in patients with Type 2 diabetes and coronary heart disease", Diabetes Care, vol. 22(9), p. 1543-1548). Therefore, measurement of AGEs may be used in combination with other markers according to the present invention for diagnosis of cardiovascular complication or risk of suffering from cardiovascular complication.

Furthermore, the methods of the present invention can also be accompanied by measurement of one or more markers chosen from the group of markers consisting of pregnancy-associated plasma protein A (PAPP-A), IL-8, IL-10, interleukin-18 (IL-18/IL-18b), ischemic modified albumin (IMA), cardiac troponin I (cTnI), cardiac troponin T (cTnT), ICAM-1 (intercellular cell adhesion molecule-1), VCAM-1 (vascular cell adhesion molecule-1), fatty acid binding protein (FABP), E-selectin, P-selectin, fibrinogen, serum amyloid A (SAA), CK-MB (creatin kinase muscle-brain), MPO (myeloperoxidase), LpPLA2 (lipoprotein-associated phospholipase A2), GP-BB (glycogen phosphorylase isoenzyme BB), IL1RA, TAFI (thrombin activable fibrinolysis inhibitor), soluble fibrin, anti-oxLDL (antibodies against oxidized low density lipoprotein), MCP-1 (monocyte chemoattractant protein-1), procoagulant tissue factor (TF), MMP-9 (matrix metalloproteinase 9), Ang-2 (angiopoietin-2), bFGF (basic fibroblast growth factor), VLDL (very low density lipoprotein), PAI-1 (plasminogen activator inhibitor-1).

The method according to the present invention comprises the step of diagnosing the risk of the patient by comparing the measured level to known levels (reference levels) associated with different grades of risk in a patient.

The person skilled in the art is able to determine known levels of markers which are associated with the "presence" or "risk" of suffering from a cardiovascular complication, particularly heart disease, microangiopathy, and/or platelet activation. Such levels can be determined according to well-known methods, as laid out, e.g., in Examples 1 and 2 or FIGS. 1 to 5. For example, the median of the measured levels in a population of patients, particularly diabetes patients, can be used to distinguish between a patient without cardiovascular complication and a patient who is suffering from a cardiovascular complication or is at risk of suffering from a cardiovascular complication. Evaluating the levels in further patients, e.g., in cohort studies, can help to refine the reference levels and to distinguish between different grades of severity of the complication or different grades of risk such as "highly increased" or "very highly increased" risk.

According to the present invention, the term "presence" in the context relates to the probability of a cardiovascular complication to be present in a given patient. The term "risk" relates to the probability of a cardiovascular complication to occur in a given patient in the future. "No risk" means that there is apparently no risk of suffering from a cardiovascular complication in the future.

The reference levels given below may serve only as a first guideline to diagnose the risk of a patient. For example, the risk of a given patient is also dependent on the spare pumping capacity of the heart of the particular patient.

Furthermore, the person skilled in the art is able to determine other reference levels from the examples shown further below.

The value of a reference level may also depend on the desired sensitivity or specificity of diagnosis. The higher the desired sensitivity, the lower is the specificity of diagnosis and vice versa. For example, a higher reference level of NT-proBNP will increase the specificity but may result in a loss of sensitivity of the diagnosis of presence or risk of suffering from a cardiovascular complication.

Typically, a plasma level of less than 33 pg/ml, particularly less than 20 pg/ml, more particularly less than 15 pg/ml, of NT-proBNP is associated with no risk of suffering from a cardiovascular complication.

Typically, a plasma level higher than 33 pg/ml, particularly higher than 125 pg/ml, more particularly higher than 500 pg/ml, of NT-proBNP is associated with a risk of suffering from a cardiovascular complication.

The higher the measured level of NT-proBNP, the higher is the risk of the patient. For example, a level of more than 1000 pg/ml indicates a highly increased risk, and a level of more than 5000 pg/ml indicates very highly increased risk.

Typically, a plasma level of less than 10 pg/ml, particularly less than 5 pg/ml, of PlGF is associated with no risk of suffering from a cardiovascular complication.

Typically, a plasma level higher than 10 pg/ml of PlGF, particularly higher than 15 pg/ml, more particularly higher than 20 pg/ml, is associated with a risk of suffering from a cardiovascular complication.

The higher the measured level of PlGF, the higher is the risk of the patient. For example, a level of more than 25 pg/ml indicates a highly increased risk, and a level of more than 30 pg/ml indicates very highly increased risk.

Once the presence or risk has been diagnosed, it may have consequences for the subsequent treatment as described below. Particularly, the present invention allows individualization of treatment according to the predominant characteristic or manifestation of diabetes. Thus, the present invention also relates to methods of treatment. "Treatment" in this context relates to any treatment which may alter the pathophysiological state of an individual and includes, for example, administering of pharmaceutical drugs as well as surgical treatment.

If a method according to the present invention indicates no risk, then treatment may be continued as planned.

If a method according to the present invention indicates a risk, then treatment may be adapted. Preferably, treatment will be accompanied by further measuring of the level of the markers of the invention and by further diagnosis, such as electrocardiography, echocardiography, or any other suitable methods known to the person skilled in the art. Furthermore, adapting treatment may include measures such as restriction of salt intake, regular moderate exercise, avoidance of non-steroidal anti-inflammatory drugs, providing influenzal and pneumococcal immunization, surgical treatment e.g., revascularization, balloon dilatation, stenting, by-pass surgery), administering drugs such as diuretics (including co-administration of more than one diuretic), ACE (angiotensin converting enzyme)-inhibitors, β-adrenergic blockers, aldosterone antagonists, calcium antagonists (calcium channel blockers), angiotensin receptor blockers, digitalis, and any other measures known and deemed appropriate by the person skilled in the art.

If a method according to the present invention indicates that the cardiovascular complication is a heart disease, then the focus of treatment will be cardiac therapy, in particular administration of ACE-inhibitors and β-adrenergic blockers. In addition, it will be desirable to avoid cardiotoxic medication and blood volume increase. Also revascularization therapy, e.g., PCTI (percutaneous therapeutic intervention), balloon dilatation, stenting, and by-pass surgery, may be considered.

ACE inhibitors are known to the person skilled in the art. Examples include benazepril, captopril, cilazapril, enalapril, fosinopril, lisinopril, moexipril, perindopril, quinapril, ramipril, spirapril, and trandolapril.

ACE inhibitors may also be able to slow down the progression of diabetic nephropathy.

β-adrenergic blockers (non-selective and PI-selective) are known to the person skilled in the art. Examples include acebutolol, alprenolol, atenolol, betaxolol, bisoprolol, bupranolol, carazolol, carteolol, carvedilol, celiprolol, metipranolol, metoprolol, nadolol, nebivolol, oxprenolol, penbutolol, pindolol, propanolol, sotalol, tanilolol, and timolol.

"Cardiotoxic medication" in this context particularly relates to administration of drugs which may lead to blood volume increase, e.g., thiazolidinedones, for example, glitazone, medione, pioglitazone, rosiglitazone, troglitazone.

If a method according to the present invention indicates that the cardiovascular complication is microangiopathy, then the focus of treatment will be medication with "lipid-lowering" drugs, e.g., statins, and/or anti-inflammatory drugs. Also administration of inhibitors or antagonists of platelet glycoprotein IIb/IIIa receptor may be considered.

Lipid-lowering drugs are known to the person skilled in the art. Examples include fibrates e.g., bezofibrate, clofibrate, etofibrate, etophylline clofibrate, fenofibrate, gemfibrozil), nicotinic acid and analogs thereof e.g., nicotinic acid, acipimox), statins e.g., simvastatin, lovastatin, pravastatin, fluvastatin, atorvastatin, cerivastatin), anion exchange resins e.g., colestyramine, colestipol), probucol, and sitosterol. Preferred lipid-lowering drugs in the present context are statins.

It is important to note that several lipid-lowering drugs, particularly statins, do also exert anti-inflammatory actions, which makes those lipid-lowering drugs further suited for treatment of microangiopathy or platelet activation.

Inhibitors or antagonists of the platelet glycoprotein IIb/IIIa receptor are known to the person skilled in the art. Examples include monoclonal or polyclonal antibodies, tirofiban, eptifibatide, and the like. In a preferred embodiment of the present invention, the glycoprotein IIb/IIIa receptor inhibitor is an antibody, in particular the antibody known under the name abciximab. Abciximab is a Fab fragment antibody which is available under the name REOPRO (Eli Lilly and Company) from Centocor Europe BV.

If a method according to the present invention indicates that the cardiovascular complication is platelet activation, then the focus of treatment will be medication with thrombocyte aggregation inhibitors and lipid-lowering drugs, e.g., statins.

Thrombocyte aggregation inhibitors are known to the person skilled in the art and include any drugs capable of inhibiting the aggregation of thrombocytes (platelets). Examples are inhibitors of cyclooxygenase, particularly COX-1, e.g., acetylsalicylic acid; ADP inhibitors, which inhibit binding of adenosine phosphate to its receptors on thrombocytes, e.g., ticlopidin or clopidogrel; inhibitors or antagonists of the platelet glycoprotein IIb/IIIa receptor (see above); dipyridamol; sulfinpyrazone; and dextran 40.

If a method according to the present invention indicates that the blood sugar level is insufficiently controlled, then the patient is treated according to any of the methods for blood sugar control known and deemed appropriate in the art. Examples include administering drugs which increase the uptake of sugar from the blood by the target tissue and administering drugs which stimulate release of insulin from pancreatic beta-cells. Examples for such well-known drugs include insulin and thiazolidinedones.

As mentioned earlier, diabetes can manifest itself in different forms. Manifestation means that the disease becomes evident by a particular complication or characteristic, e.g., cardiovascular complication, heart disease, microangiopathy, platelet activation, inflammation, or insufficient control of the blood sugar level. Due to individual differences, such as genetic differences, different lifestyles, e.g., alcohol or nicotine abuse and lack of physical exercise, or a different disease history, diabetes can manifest itself through different complications or characteristics in each individual patient. For example, a particular patient may suffer from heart disease, whereas a different patient suffers from microangiopathy or diabetic nephropathy. As another example, a patient in whom blood sugar level is not sufficiently controlled may not be suffering from microangiopathy due to the fact that the patient has not been suffering from diabetes for a long time, whereas a patient who has been suffering from diabetes for many years may be suffering from microangiopathy even though his blood sugar level is relatively well controlled.

Therefore, the method according to the present invention may comprise the diagnosis of a manifestation, particularly the predominant manifestation, of diabetes belonging to the group consisting of cardiovascular complication, heart disease, microangiopathy, platelet activation, inflammation, and insufficient control of the blood sugar level.

From the above, it is clear that the invention also relates to a method for determining manifestation, particularly the predominant manifestation of diabetes in a patient, comprising the steps of a. measuring, preferably in vitro, the level(s) of at least one cardiac hormone or a variant thereof in a sample from the patient, and b. preferably additionally measuring the level(s) of at least one angiogenesis marker or a variant thereof in a sample from the patient, and c. preferably additionally measuring the level(s) of at least one marker for platelet activation or a variant thereof in a sample from the patient, and d. preferably additionally measuring the level(s) at least one marker chosen from the group consisting of CRP, hsCRP, IL-6, or a variant thereof, in a sample from the patient, and e. preferably additionally measuring the level(s) at least one marker chosen from the group consisting of glucose, HbA1c, CML, and AGE, in a sample from the patient, and f. diagnosing the manifestation by comparing the measured level(s) to known level(s) associated with the manifestation, wherein g. the level of the marker(s) according to step a) to c) are indicative that the manifestation is cardiovascular complication or risk of suffering from a cardiovascular complication, and h. the level of the marker(s) according to step a) is indicative that the manifestation is microangiopathy or risk of suffering from microangiopathy, and i. the level of the marker(s) according to step b) is indicative that the manifestation is heart disease or risk of suffering from heart disease, and j. the level of the marker(s) according to step c) is indicative that the manifestation is platelet activation or risk of suffering from platelet activation, and k. the level of the marker(s) according to step d) is indicative that the manifestation is inflammation or risk of suffering from inflammation, and l. the level of the marker(s) according to step e) is indicative that the manifestation is insufficient control of the blood sugar level.

As mentioned earlier, the level of the marker(s) according to step b is furthermore indicative that the manifestation is diabetic nephropathy, diabetic retinal damage, hypoxia of extremities, or risk of suffering from diabetic nephropathy, diabetic retinal damage, or hypoxia of extremities.

Again, as mentioned earlier, the level of the marker(s) according to step c is furthermore indicative that the manifestation is platelet aggregation, thrombus formation, thrombus propagation, the risk that a plaque having already become vulnerable will rupture, UAP, AMI, or risk of suffering from platelet aggregation, thrombus formation, thrombus propagation, the risk that a plaque having already become vulnerable will rupture, UAP, or AMI.

Determination will be the better the more additional markers according to the preferred steps b to e of the above method are measured.

The present invention relates not only to methods of diagnosis, but also to the use of the markers according to the present invention for diagnosis.

Diagnosis according to the present invention is preferably done by use of a diagnostic means. A diagnostic means is any means that allows to measure the level, amount, or concentration of a substance of interest, particularly a peptide or polypeptide of interest.

Peptides or polypeptides of interest according to the present invention are the biochemical markers as described in this specification.

Methods and diagnostic means which can be used to determine the levels of the respective peptides are known to the person skilled in the art. These methods include microplate ELISA-based methods, fully-automated or robotic immunoassays (available for example on ELECSYS analyzers), CBA (an enzymatic cobalt binding assay, available, for example, on Roche/Hitachi analyzers), and latex agglutination assays (available for example on Roche/Hitachi analyzers).

Furthermore, the person skilled in the art is familiar with different methods of measuring the level of a peptide or polypeptide. The term "level" relates to amount or concentration of a peptide or polypeptide in a patient or a sample taken from a patient.

The term "measuring" according to the present invention relates to determining the amount or concentration, preferably semi-quantitatively or quantitatively, of the nucleic acid, peptide, polypeptide, or other substance of interest. Measuring can be done directly or indirectly. Indirect measuring includes measuring of cellular responses, bound ligands, labels, or enzymatic reaction products.

In the context of the present invention, amount also relates to concentration. It is evident that, from the total amount of a substance of interest in a sample of known size, the concentration of the substance can be calculated and vice versa.

Measuring can be done according to any method known in the art, such as cellular assays, enzymatic assays, or assays based on binding of ligands. Preferred methods are described in the following.

In another preferred embodiment, the method for measuring the level of a peptide or polypeptide of interest comprises the steps of (a) contacting a peptide or polypeptide with a suitable substrate for an adequate period of time, and (b) measuring the amount of product.

In another preferred embodiment, the method for measuring the level of a peptide or polypeptide of interest comprises the steps of (a) contacting a peptide or polypeptide with a specifically binding ligand, (b) (optionally) removing non-bound ligand, and (c) measuring the amount of bound ligand.

Preferably, the peptide or polypeptide is contained in a sample, particularly a body fluid or tissue sample, and the amount of the peptide or polypeptide in the sample is measured.

Peptides and polypeptides (proteins) can be measured in tissue, cell, and body fluid samples, i.e., preferably in vitro. Preferably, the peptide or polypeptide of interest is measured in a body fluid sample.

A tissue sample according to the present invention refers to any kind of tissue obtained from the dead or alive human or animal body. Tissue samples can be obtained by any method known to the person skilled in the art, for example, by biopsy or curettage.

Body fluids according to the present invention may include blood, blood serum, blood plasma, lymph, cerebral liquor, saliva, vitreous humour, and urine. Particularly, body fluids include blood, blood serum, blood plasma, and urine. Samples of body fluids can be obtained by any method known in the art. Preferably, the sample is blood, blood serum, or blood plasma.

If necessary, the samples may be further processed. Particularly, nucleic acids, peptides or polypeptides may be purified from the sample according to methods known in the art, including filtration, centrifugation, or extraction methods such as chloroform/phenol extraction.

Other preferred methods for measurement may include measuring the amount of a ligand binding specifically to the peptide or polypeptide of interest. Binding according to the present invention includes both covalent and non-covalent binding.

A ligand according to the present invention can be any peptide, polypeptide, nucleic acid, or other substance binding to the peptide or polypeptide of interest. It is well known that peptides or polypeptides, if obtained or purified from the human or animal body, can be modified, e.g., by glycosylation. A suitable ligand according to the present invention may bind the peptide or polypeptide also via such sites.

Preferably, the ligand should bind specifically to the peptide or polypeptide to be measured. "Specific binding" according to the present invention means that the ligand should not bind substantially to ("cross-react" with) another peptide, polypeptide, or substance present in the sample investigated. Preferably, the specifically bound protein or isoform should be bound with at least 3 times higher, more preferably at least 10 times higher, and even more preferably at least 50 times higher affinity than any other relevant peptide or polypeptide.

Non-specific binding may be tolerable, particularly if the investigated peptide or polypeptide can still be distinguished and measured unequivocally, e.g., by separation according to its size, e.g., by electrophoresis, or by its relatively higher abundance in the sample.

Binding of the ligand can be measured by any method known in the art. Preferably, the method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured, e.g., the amount of a protease can be measured by measuring the amount of cleaved substrate, e.g., on a western blot.

For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable amount of product to be produced. Instead of measuring the amount of product, the time necessary for appearance of a given, e.g., detectable, amount of product can be measured.

Third, the ligand may be coupled covalently or non-covalently to a label, allowing detection and measurement of the ligand.

Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary, or even higher order ligands is often used to increase the signal. Suitable secondary and higher order ligands may include antibodies, secondary antibodies, and the well-known streptavidin-biotin system (Vector Laboratories, Inc.)

The ligand or substrate may also be "tagged" with one or more tags as known in the art. Such tags may then be targets for higher order ligands. Suitable tags include biotin, digoxigenin, his-tag, glutathione-S-transferase, FLAG, GFP, myc-tag, influenza A virus haemagglutinin (HA), maltose binding protein, and the like. In the case of a peptide or polypeptide, the tag is preferably at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels, e.g., "magnetic beads", including paramagnetic and superparamagnetic labels, and fluorescent labels.

Enzymatically active labels include, e.g., horseradish peroxidase, alkaline phosphatase, beta-galactosidase, luciferase, and derivatives thereof. Suitable substrates for detection include diaminobenzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-STAR (Amersham Biosciences), and ECF (Amersham Biosciences). A suitable enzyme-substrate combination may result in a colored reaction product, fluorescence, or chemiluminescence which can be measured according to methods known in the art, e.g., using a light-sensitive film or a suitable camera system. As for measuring the enzymatic reaction, the criteria given above apply analogously.

Typical fluorescent labels include fluorescent proteins (such as GFP and its derivatives), Cy3, Cy5, Texas Red, Fluorescein, and the Alexa dyes, e.g., Alexa 568. Further fluorescent labels are available, e.g., from Molecular Probes, Oreg. Also, the use of quantum dots as fluorescent labels is contemplated.

Typical radioactive labels include $^{35}S$, $^{125}I$, $^{32}P$, $^{33}P$, and the like. A radioactive label can be detected by any method known and appropriate, e.g., a light-sensitive film or a phosphor imager.

Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoroimmunoassay (DELFIA), scintillation proximity assay (SPA), turbidimetry, nephelometry, latex-enhanced turbidimetry or nephelometry, solid phase immune tests, and mass spectrometry such as SELDI-TOF, MALDI-TOF, or capillary electrophoresis-mass spectrometry (CE-MS). Further methods known in the art, such as gel electrophoresis, 2D gel electrophoresis, SDS polyacrylamide gel electrophoresis (SDS-PAGE), and western blotting, can be used alone or in combination with labeling or other detection methods as described above.

Preferred ligands include antibodies, nucleic acids, peptides or polypeptides, and aptamers, e.g., nucleic acid or peptide aptamers. Methods for using such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides, or polypeptides. These derivatives can then be tested for binding according to screening procedures known in the art, e.g., phage display.

The term "antibody" as used herein includes both polyclonal and monoclonal antibodies as well as fragments thereof, such as Fv, Fab, and $F(ab)_2$ fragments that are capable of binding antigen or hapten.

In another preferred embodiment, the ligand, preferably chosen from the group consisting of nucleic acids, peptides, and polypeptides, more preferably from the group consisting of nucleic acids, antibodies, and aptamers, is present on an array. Said array contains at least one additional ligand, which may be directed against a peptide, polypeptide, or a nucleic acid of interest. Said additional ligand may also be directed against a peptide, polypeptide, or a nucleic acid of no particular interest in the context of the present invention. Preferably, ligands for at least three, preferably at least five, more preferably at least eight peptides or polypeptides of interest in the context of the present invention are contained on the array.

According to the present invention, the term "array" refers to a solid-phase or gel-like carrier upon which at least two compounds are attached or bound in one-, two- or three-dimensional arrangement. Such arrays (including "gene chips", "protein chips", antibody arrays, and the like) are generally known to the person skilled in the art and typically generated on glass microscope slides, specially coated glass slides such as polycation-, nitrocellulose- or biotin-coated slides, cover slips, and membranes such as, for example, membranes based on nitrocellulose or nylon.

The array may include a bound ligand or at least two cells expressing each at least one ligand.

It is also contemplated to use "suspension arrays" as arrays according to the present invention (Nolan J P, Sklar L A, 2002, "Suspension array technology: evolution of the flat-array paradigm", Trends Biotechnol. 20(1):9-12). In such suspension arrays, the carrier, e.g., a microbead or microsphere, is present in suspension. The array consists of different microbeads or microspheres, possibly labeled, carrying different ligands.

The invention further relates to a method of producing arrays as defined above, wherein at least one ligand is bound to the carrier material in addition to other ligands.

Methods of producing such arrays, for example, based on solid-phase chemistry and photo-labile protective groups, are generally known (U.S. Pat. No. 5,744,305). Such arrays can also be brought into contact with substances or substance libraries and tested for interaction, for example, for binding or change of confirmation. Therefore, arrays comprising a peptide or polypeptide as defined above may be used for identifying ligands binding specifically to said peptides or polypeptides.

EXAMPLES

Example 1

Study Design

The study design and main results of the Steno-2 study have previously been reported in detail (Gaede, P., Vedel, P., Larsen, N. et al., 2003, "Multifactorial intervention and cardiovascular disease in patients with Type 2 diabetes", New England Journal of Medicine, vol. 348 (5), pp. 383-93). In brief, 160 microalbuminuric Type 2 diabetic patients were randomized to conventional (n=80) or intensified multifactorial treatment targeting several concomitant risk factors. Patients in the intensive therapy group were treated with a stepwise introduction of lifestyle and pharmacologic interventions intended to maintain glycosylated hemoglobin values below 6.5%, blood pressure below 130/80 mm Hg, fasting serum total cholesterol levels below 175 mg/dl, and fasting serum triglyceride levels below 150 mg/dl. Recommended lifestyle interventions included reduced intake of dietary fat, regular participation in light or moderate exercise, and cessation of smoking. All participants in the intensive therapy group were also advised to take low dose aspirin and an angiotensin-converting enzyme (ACE) inhibitor, regardless of blood pressure level. Mean follow-up was 7.8 years. Throughout the study period, the intensive group had significantly lower values of $HbA_{1c}$, fasting serum levels of total cholesterol, LDL-cholesterol, and triglycerides, systolic and diastolic blood pressure, and urinary albumin excretion rate (Gaede, supra). These changes were associated with significant reductions in the risk for macrovascular as well as microvascular disease (relative risk reduction 53% for cardiovascular disease, 61% for progression to nephropathy, 58% for progression in retinopathy, and 63% for progression in autonomic neuropathy) (Gaede, supra).

All 160 participating patients were recruited from the Steno Diabetes Center during 1992-93. Microalbuminuria was defined as a urinary albumin excretion rate (AER) of 30-300 mg per 24 h in four of six 24 h urine samples. Diabetes was defined by 1985 WHO criteria. Exclusion criteria were age older than 65 or younger than 40 years; a stimulated serum C-peptide concentration less than 600 pmol/l 6 min after intravenous injection of 1 mg of glucagon; pancreatic insufficiency or diabetes secondary to pancreatitis; alcohol abuse; non-diabetic kidney disease; malignancy; or life-threatening disease with death probable within 4 years. Informed consent was obtained from all participants. The protocol was in accordance with the Helsinki declaration and was approved by the ethics committee of Copenhagen County.

In the present post-hoc analysis, patients were stratified into two groups according to baseline plasma NT-proBNP below the median or above the median levels of the cohort.

Endpoints

The primary endpoint in the study was a combined endpoint for cardiovascular disease comprising cardiovascular mortality, non fatal myocardial infarction, non-fatal stroke, percutaneous coronary interventions, coronary artery bypass graft, vascular surgery, and amputations. A secondary endpoint comprising cardiovascular mortality and admission for congestive heart failure was also examined.

Assays

All blood samples were taken at 0800 after an overnight fast. Patients did not take their drugs in the morning of the day of blood sampling.

After the patients had been at rest for at least 20 minutes in the supine position, blood samples for analysis of plasma NT-proBNP were collected, centrifuged and plasma stored at −80° C. until analysis. Plasma concentrations of NT-proBNP were measured by a sandwich immunoassay on an ELECSYS 2010 analyzer (Roche Diagnostics GmbH, Germany). The analytical range extends from 5 to 35 000 pg/ml, and the total coefficient of variation is <0.061 in pooled human plasma samples. To convert from pg/ml to pmol/l, multiply by 0.118. Blood samples were taken at baseline and after two, four, and eight years of follow-up.

Statistics

Comparison of groups at baseline was by one-way analysis of variance or Mann-Whitney test whenever appropriate for numerical variables. Chi-squared test or Fisher's exact test was used to compare categorical variables.

Since the two original treatment groups differed significantly in the risk for cardiovascular disease, the role of plasma NT-proBNP as a risk marker for cardiovascular disease was analyzed in each of these groups separately using the median value within each of the original treatment groups as cut-off for the below or above the median group as well as in a combined group.

Event curves for the time to the first event for the primary and secondary endpoints were based on Kaplan-Meier analysis, and the two groups were compared using the log-rank test. Hazard ratios with 95% confidence intervals were calculated using a Cox regression model. Results are presented both unadjusted as well as two models with adjustments for risk factors for cardiovascular disease in patients with Type 2 diabetes; Model 1 with adjustments for known diabetes duration, known cardiovascular disease at baseline, gender and age as previously reported, and Model 2 with further adjustments for systolic and diastolic blood pressure, glycosylated hemoglobin A1c, fasting serum total cholesterol, HDL-cholesterol, LDL-cholesterol, triglycerides, and urinary albumin excretion rate. Results for the combined cohort were also adjusted for original treatment allocation. Changes in the plasma NT-proBNP level during time within each of the two treatment groups were compared with the Wilcoxon test.

Results

The range of fasting plasma levels of NT-proBNP at baseline was 5 (lowest detectable value) to 1290 pg/ml with a median value of 33.5 pg/ml in the entire Steno-2 cohort, whereas values in the original intensive therapy group was from 5 to 1290 (median 35.3) pg/ml and in the conventional therapy group from 5 to 1134 (median 32.0) pg/ml. Baseline characteristics of the two groups are shown in Table 1. High baseline plasma NT-proBNP level was associated with longer diabetes duration, higher age, higher systolic blood pressure and impaired kidney function. Similarly, a higher proportion of patients in the above median group was treated with calcium antagonists at baseline (Table 1).

TABLE 1

Baseline characteristics of 160 Type 2 diabetic patients according to baseline plasma N-terminal proBNP level below or above the median in the entire cohort

|  | Below median group N = 80 | Above median group N = 80 | p-value |
|---|---|---|---|
| HbA1c (%)* | 8.7 (0.2) | 8.4 (0.2) | 0.29 |
| Systolic BP (mm Hg)* | 143 (1.9) | 153 (2.2) | 0.002 |
| Diastolic BP (mm Hg)* | 86 (1.0) | 85 (1.3) | 0.39 |
| Fasting serum total cholesterol (mg/dl)* | 224 (4) | 209 (4) | 0.048 |
| Fasting serum HDL-cholesterol (mg/dl)* | 40 (1) | 39 (1) | 0.62 |
| Fasting serum triglyceride (mg/dl)† | 186 (62-992) | 168 (44-1993) | 0.09 |
| Known diabetes duration (yr)† | 5 (0-26) | 7 (0-30) | 0.003 |
| Gender (n) | 59 ♂/21 ♀ | 60 ♂/20 ♀ | 0.96 |
| Smokers (n) | 28 | 32 | 0.55 |
| Serum creatinine (μmol/l)* | 74 (1.5) | 80 (2.1) | 0.015 |
| Weight (kg)* | 92.8 (1.7) | 89.1 (1.8) | 0.13 |
| Glomerular filtration rate (ml/min/1.73 m$^2$)* | 125 (2.4) | 109 (2.8) | <0.0001 |
| Known cardiovascular disease (n) | 7 | 14 | 0.11 |

TABLE 1-continued

Baseline characteristics of 160 Type 2 diabetic patients according to baseline plasma N-terminal proBNP level below or above the median in the entire cohort

|  | Below median group N = 80 | Above median group N = 80 | p-value |
|---|---|---|---|
| Left ventricular mass index* | 110 (2.9) | 126 (4.2) | 0.001 |
| Age (yr)* | 52 (0.8) | 58 (0.7) | <0.0001 |
| NT-proBNP (pg/ml)† | 13.0 (<5-32.8) | 69.7 (33.5-1290) | <0.0001 |
| Urinary albumin excretion (mg/24 h)† | 70 (32-286) | 80 (33-265) | 0.11 |
| Urinary sodium excretion (mmol/24 h)† | 213 (46-577) | 176 (25-449) | 0.19 |
| Medication: | | | |
| ACE-inhibitors (n) | 13 | 18 | 0.42 |
| Diuretics (n) | 14 | 25 | 0.07 |
| Beta-blockers (n) | 4 | 5 | 1.00 |
| Calcium-blockers (n) | 3 | 13 | 0.02 |
| Treatment allocation | 41 intensive | 39 intensive | 0.69 |

*Mean (SE), †median (range)

To convert values for cholesterol to mmol/l, multiply by 0.02586. To convert values for triglycerides to mmol/l, multiply by 0.01129. To convert values for NT-proBNP to pmol/l, multiply by 0.118.

During a mean follow-up time of 7.8 years, 12 major cardiovascular events were seen in the group with plasma NT-proBNP below the median value compared to 54 events in the above the median group, p<0.0001 (FIG. 1). Similarly, the significant correlation between cardiovascular disease and the plasma NT-proBNP level was also observed in each of the two original treatment groups in the Steno-2 study as shown in Table 1. Adjustment for risk factors for cardiovascular disease in Type 2 diabetes did not change the significance of the correlation in any of the adjustment models (Table 2). Table 2 shows the hazard ratio (95% CI) for the primary and secondary endpoints in Type 2 diabetic patients with plasma NT-proBNP levels above the median compared to patients with plasma levels below the median (panel A), or using a cut-off level of 125 pg/ml (panel B). Model 1 is adjusted for known cardiovascular disease at baseline, known diabetes duration, age, and gender. Model 2 adjusted for variables in Model 1 as well as systolic and diastolic blood pressure, glycosylated hemoglobin A1c, fasting serum lipids, and urinary albumin excretion rate.

TABLE 2

|  | Intensive group | Conventional group | Combined group |
|---|---|---|---|
| Panel A | | | |
| Primary endpoint | | | |
| Unadjusted | 6.1 (1.8-20.9) p = 0.004 | 3.1 (1.5-6.5) p = 0.002 | 4.4 (2.3-8.4) p < 0.0001 |
| Model 1 | 4.7 (1.2-17.7) p = 0.022 | 2.3 (1.0-5.0) p = 0.0138 | 3.3 (1.7-6.5) p = 0.001 |
| Model 2 | 4.1 (1.0-16.7) p = 0.048 | 3.0 (1.2-7.6) p = 0.021 | 3.6 (1.7-7.5) p = 0.001 |
| Secondary endpoint | | | |
| Unadjusted | 7.3 (0.9-59.3) p = 0.06 | 3.3 (1.1-10.2) p = 0.0136 | 5.8 (2.0-16.9) p = 0.001 |
| Model 1 | 4.4 (0.4-48.2) p = 0.23 | 3.3 (0.9-12.3) p = 0.08 | 4.4 (1.3-14.3) p = 0.015 |

TABLE 2-continued

|  | Intensive group | Conventional group | Combined group |
|---|---|---|---|
| Model 2 | 3.0 (0.3-32.7) p = 0.138 | 5.2 (1.0-26.1) p = 0.044 | 8.4 (2.0-36.3) p = 0.004 |
| Panel B | | | |
| Primary endpoint | | | |
| Unadjusted | 6.0 (2.3-15.3) p = 0.0002 | 3.4 (1.8-8.0) p = 0.001 | 4.7 (2.6-8.4) p < 0.0001 |
| Model 1 | 5.7 (2.0-16.3) p = 0.001 | 2.4 (1.0-5.6) p = 0.048 | 3.0 (1.6-5.7) p = 0.001 |
| Model 2 | 7.1 (1.9-27.1) p = 0.004 | 2.9 (1.0-8.6) P = 0.047 | 3.3 (1.7-6.7) p = 0.001 |
| Secondary endpoint | | | |
| Unadjusted | 8.7 (2.2-34.9) p = 0.002 | 4.1 (1.5-11.2) p = 0.007 | 5.3 (2.4-12.0) p < 0.0001 |
| Model 1 | 7.4 (1.5-37.2) p = 0.015 | 2.9 (0.9-9.4) p = 0.08 | 3.4 (1.4-8.2) p = 0.006 |
| Model 2 | 15.1 (1.0-238.0) p = 0.054 | 2.4 (0.6-10.0) p = 0.24 | 4.5 (1.5-13.5) p = 0.007 |

Figure 2:
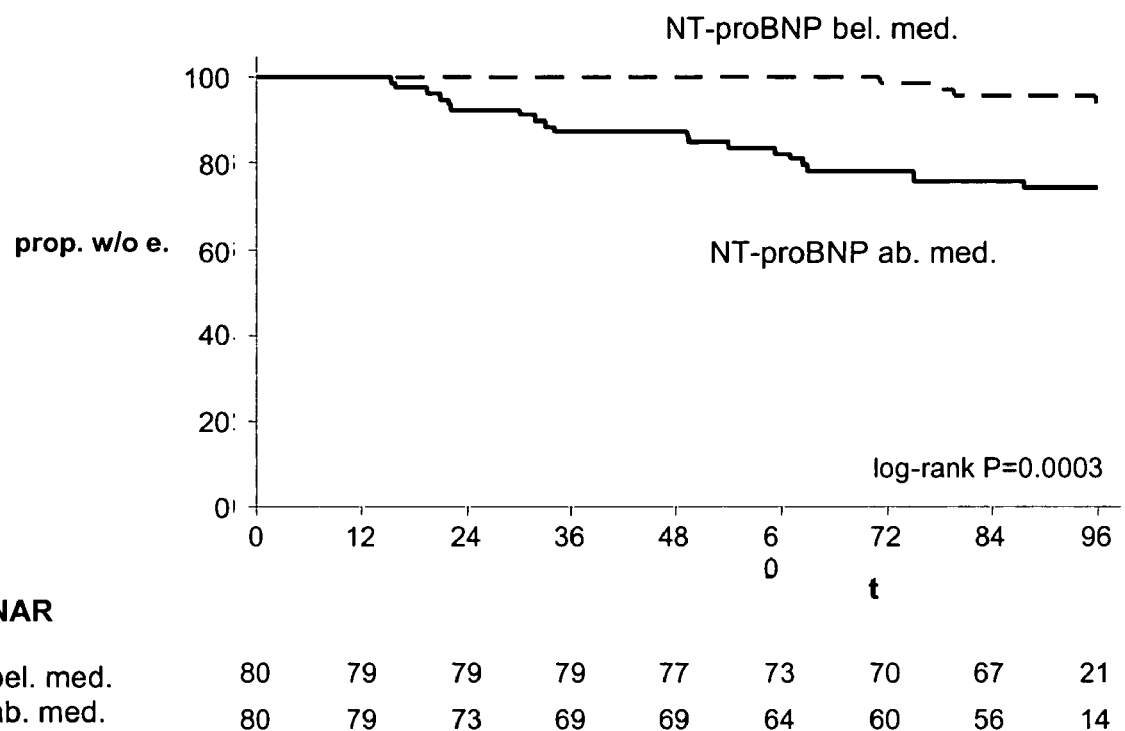
FIG. 2 shows a Kaplan-Meier plot of time to death from cardiovascular disease or first admission for congestive heart failure in Type 2 diabetic patients with baseline plasma NT-proBNP concentrations below (dashed line) or above the median in the entire cohort. P-value calculated with log-rank test. Prop. w/o e., Proportion without events; t, time (months); NAR, number at risk; bel. med., below median group; ab. med., above median group.

The hazard ratio for the secondary endpoint was also significantly correlated to the baseline level of plasma NT-proBNP, both unadjusted and adjusted for classical risk factors (FIG. 2). However, although hazard ratios of a similar magnitude were observed when analyzed in each of the two original treatment groups, adjustment diluted the significance of plasma NT-proBNP as a risk marker (Table 2).

In a setting applying a cut-off level of plasma NT-proBNP of 125 pg/ml, the significance and size of the risk for the primary and secondary endpoints did not change substantially compared to the lower cut-off level in the present cohort (Table 2).

Figure 3:
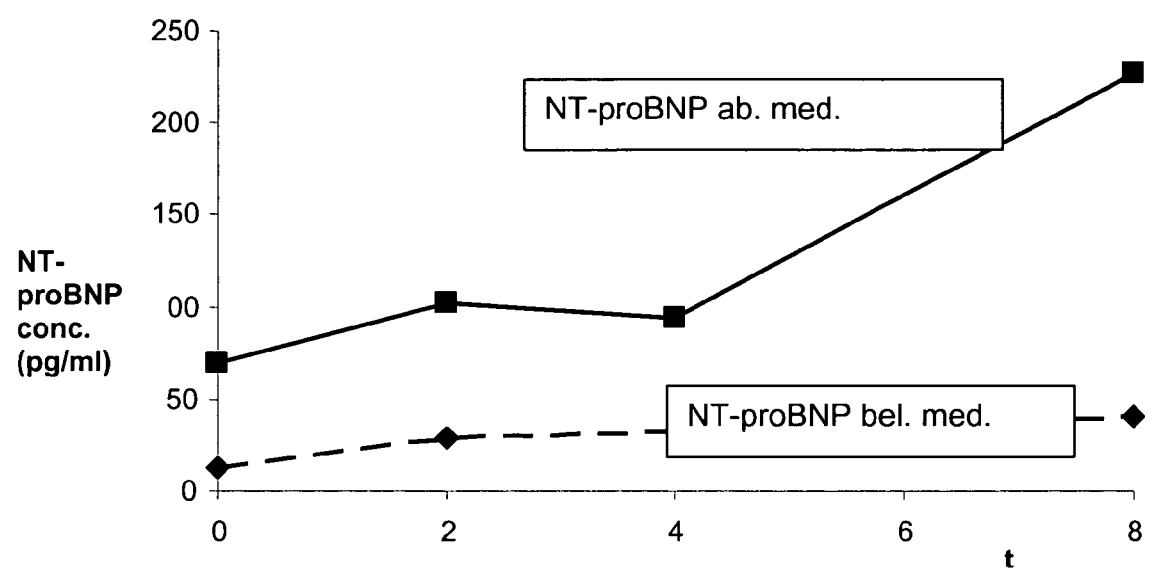
FIG. 3 shows median plasma levels of NT-proBNP during follow-up in patients with plasma NT-proBNP below (dashed line) or above the median in the cohort of 160 Type 2 diabetic patients in the Steno-2 study. conc., concentration; t, time (years); ab. med., above median group; bel. med., below median group.
Figure 4:
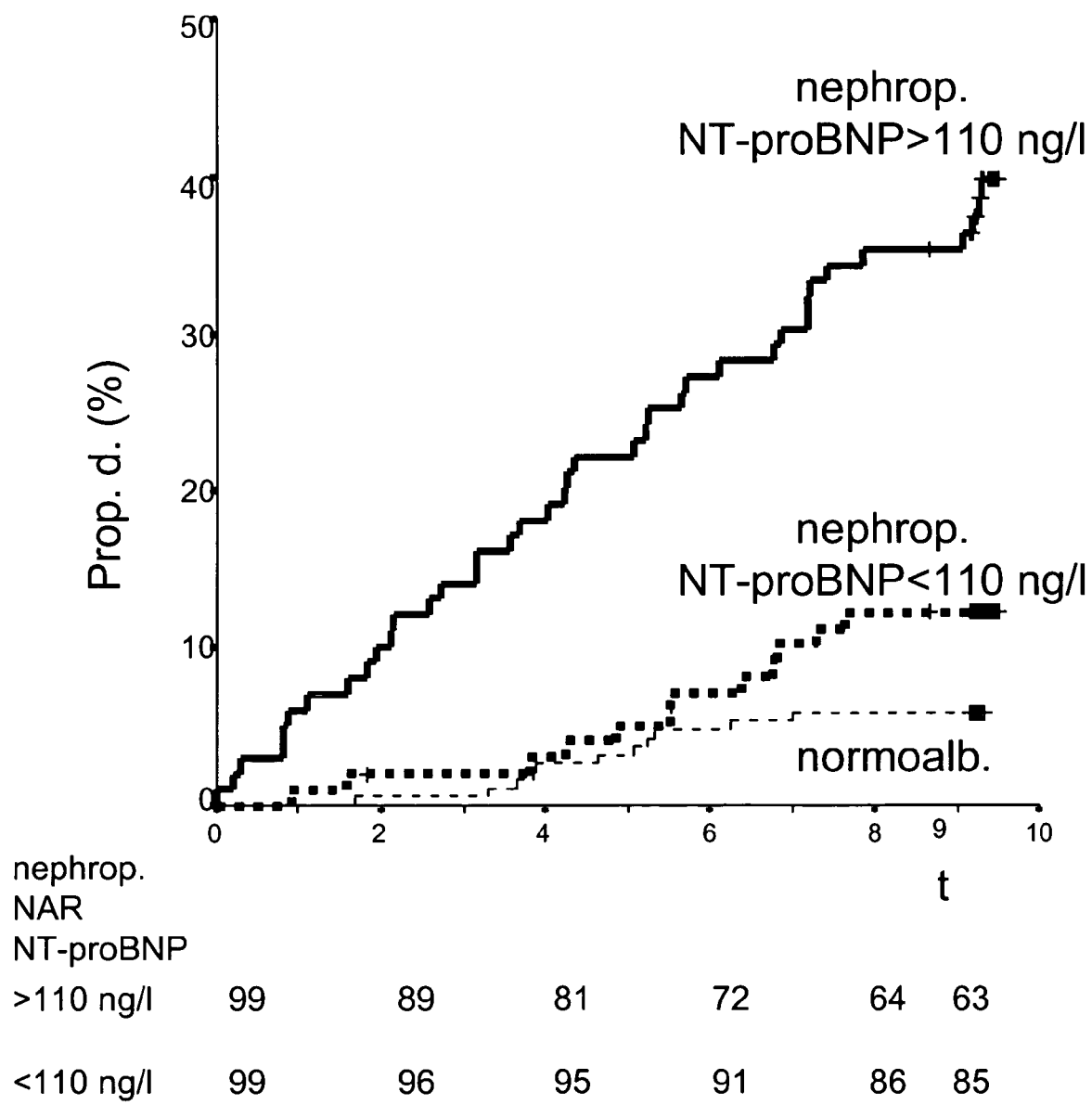
FIG. 4 shows Kaplan-Meier curves of all cause mortality in patients with diabetic nephropathy and NT-proBNP concentration above versus below the median value (110 ng/l)—Log rank test, $p<0.0001$. For comparison the curve for normoalbuminuric patients is shown in thin line. Prop. d., proportion died; t, follow-up period (years); nephrop., nephropathy; normalb., normoalbuminuria, NAR, numbers at risk.
Figure 5:
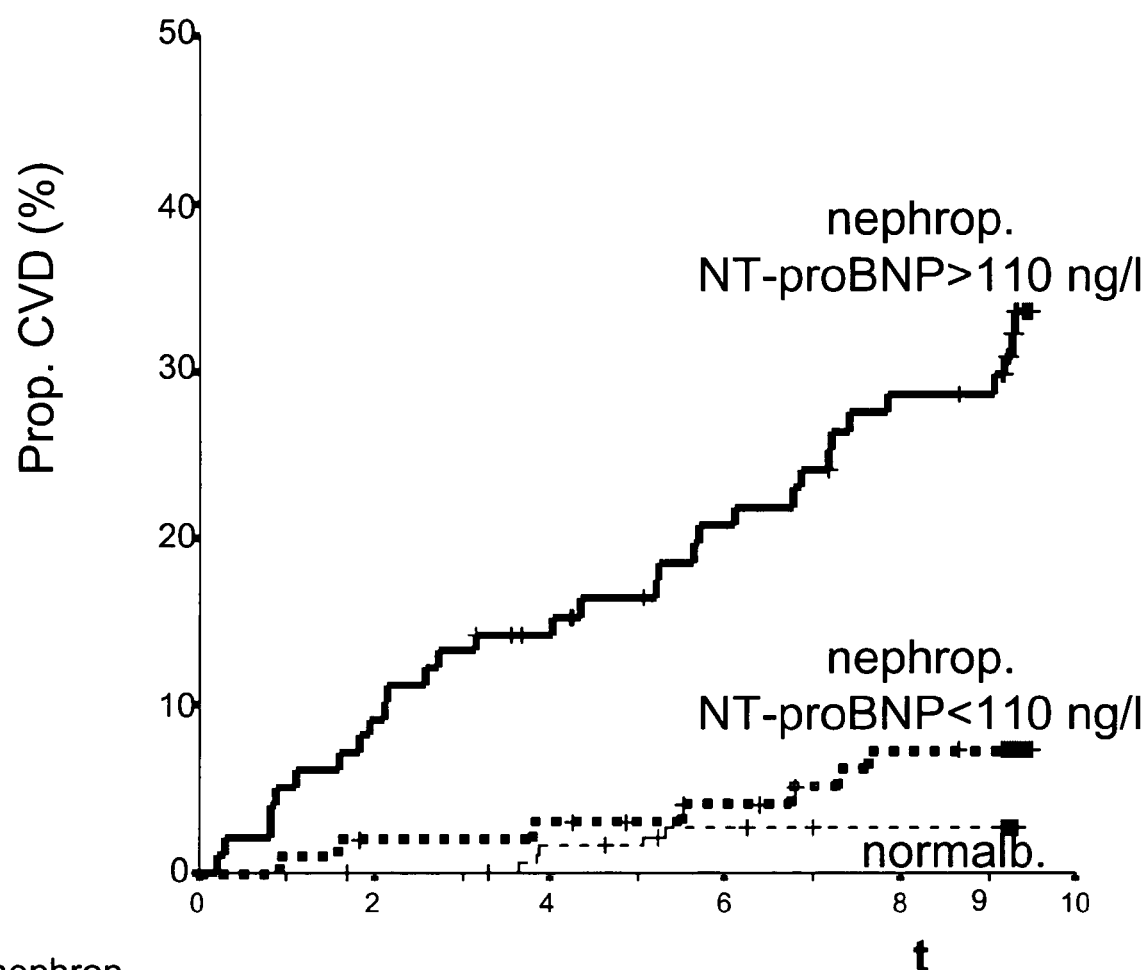
FIG. 5 shows Kaplan-Meier curves of cardiovascular mortality in patients with diabetic nephropathy and NT-proBNP concentration above versus below the median value (110 ng/l)—Log rank test, $p<0.0001$. For comparison the curve for normoalbuminuric patients is shown in thin line. Prop. CVD, proportion with cardiovascular death; t, follow-up period (years); nephrop., nephropathy; normalb., normoalbuminuria, NAR, numbers at risk.

When measured two years after study, start levels of plasma NT-proBNP increased significantly in the combined cohort with 14.9 pg/ml, p<0.0001, and a similar result was seen in the intensive and the conventional therapy group (11.7 pg/ml, p=0.001, and 18.2 pg/ml, p<0.0001, respectively). Median plasma NT-proBNP levels continued to increase in both the below and above median group during follow-up as shown in FIG. 3. This was also the case when the original intensified therapy group and the conventional therapy group was analyzed separately.

Changes in plasma NT-proBNP during the first two years of intervention were significantly correlated with the risk for cardiovascular events during the rest of the follow-up period. A 10 pg/ml reduction in the plasma NT-proBNP level in the combined cohort was associated with a significant 1% relative risk reduction in both the intensive, conventional, and combined cohort for the primary as well as for the secondary endpoint (p<0.001 in all cases). A total of 42 patients reduced plasma NT-proBNP levels during the first two years of follow-up with a median decrease of 12 pg/ml. Eighteen patients from the baseline classification above the median reached the below median level after 2 years of intervention. Reaching this level was, however, not associated with a decreased risk for cardiovascular disease compared to patients not reaching the level (hazard ratio 0.45 (0.12-1.65, p=0.23)).

The correlation between the plasma NT-proBNP level and risk for cardiovascular disease during the remaining follow-up period remained significant after 2 years for both the primary and the secondary endpoint.

In the present post-hoc analysis from the Steno-2 study, we have demonstrated a significant and independent correlation between plasma NT-proBNP levels and the future risk for cardiovascular disease as well as for a secondary endpoint comprising cardiovascular mortality and admission for congestive heart failure in patients with Type 2 diabetes and microalbuminunia.

In conclusion, the role of plasma NT-proBNP as a strong risk marker for cardiovascular disease and congestive heart failure exists in patients with Type 2 diabetes.

Example 2

Patients and Study Design

During 1993, all Type 1 diabetic patients with diabetic nephropathy (n=242) attending the outpatient clinic at Steno Diabetes Center, in whom glomerular filtration rate had been measured during the same year, were invited to participate in a case-control study (Tarnow, L., Cambien, F., et al., 1995, "Insertion/deletion polymorphism in the angiotensin-I-converting enzyme gene is associated with coronary heart disease in IDDM patients with diabetic nephropathy", Diabetologica, vol. 38, pp. 798-803). A total of 199 patients fulfilling the clinical criteria for diabetic nephropathy (persistent macroalbuminuria (>300 mg/24 h) in at least two out of three consecutive 24-hour urine collections, in the presence of diabetic retinopathy and the absence of other kidney or urinary tract disease (Parving H-H, Østerby R, Ritz E., "Diabetic nephropathy", in Brenner B M, ed., The Kidney, pp. 1777-818, Philadelphia, W B Saunders, 2003) were recruited. A group of 192 patients with long lasting Type 1 diabetes and persistent normoalbuminuria served as controls. Plasma NT-proBNP was measured in 198 patients with nephropathy and in 188 patients with normoalbuminuria.

In a prospective observational study, design the patients were followed up till Feb. 1, 2003, or until death (n=62) or emigration (n=3). The study was approved by the local ethics committee, in accordance with the Helsinki Declaration, and all patients gave their informed written consent.

Baseline Clinical and Laboratory Investigations

Investigations were performed in the morning after an overnight fast. No antihypertensive medication was ever prescribed in 24% of patients with nephropathy and 88% of the normoalbuminuric patients. All of the remaining patients were asked to stop their antihypertensive and diuretic treatment 8 days before the examination. Not all patients, however, wanted to do so, and thus 34% and 4% of patients in the nephropathy and normoalbuminuria group, respectively, had taken antihypertensive medication at the day of examination.

Arterial blood pressure was measured twice with an appropriate cuff size following at least 10 minutes rest in the supine position. Urinary albumin concentration was measured by an enzyme immunoassay (Feldt-Rasmussen B, Dinesen B, Deckert M., "Enzyme immunoassay: an improved determination of urinary albumin in diabetics with incipient nephropathy", Scand. J. Clin. Lab. Invest., 1985, 45:539-44) from 24 h urine collections. Serum creatinine concentration was assessed by a kinetic Jaffé method. Glomerular filtration rate was measured in patients with diabetic nephropathy after a single injection of 3.7 MBq $^{51}$Cr-EDTA by determination of radioactivity in venous blood samples taken 180, 200, 220, and 240 minutes after the injection. In normoalbuminuric patients, glomerular filtration rate was estimated by the Modification of Diet in Renal Disease (MDRD) equation (Levey A S, Bosch J P, Lewis J B, Greene T, Rogers N, Roth D, et al., "A more accurate method to estimate glomerular filtration rate from serum creatinine: a new prediction equation", Ann. Intern. Med., 1999, 130:461-70). Diabetic retinopathy was assessed in all patients by fundus photography after papillary dilatation and graded as nil, simplex, or proliferative retinopathy. Patients were interviewed using the WHO cardiovascular questionnaire. Major cardiovascular events were diagnosed as a history of stroke and/or myocardial infarction. Smoking was defined as persons smoking one or more cigarettes/cigars/pipes a day, all others were classified as non-smokers.

Measurements of NT-proBNP

After the patients had been at rest for at least 20 minutes in the supine position, blood samples for determination of NT-proBNP were collected, centrifuged, and plasma stored at −80° C. until analysis. Plasma concentrations of NT-proBNP were measured by a sandwich immunoassay on an ELECSYS 2010 analyzer (Roche Diagnostics GmbH, Germany). The intra-assay variation is below 3.0% and the total coefficient of variation ranges between 2.2 and 5.8% in low and high ranges of NT-proBNP.

Follow-Up

All patients were traced through the national register during the summer of 2003. If a patient had died before Feb. 1, 2003, the date of death was recorded, and information on the cause of death obtained from the death certificate. All death certificates were reviewed independently by two observers, and the primary cause of death recorded. Additional available information from necropsy reports was included. All deaths were classified as cardiovascular deaths unless an unequivocal non-cardiovascular cause was established (Pfeffer M A, Swedberg K, Granger C P, Held P, McMurray J J V, Michelson E L et al., "Effects of candesartan on mortality and morbidity in patients with chronic heart failure: the CHARM-overall programme", Lancet 2003, 362:759-66).

Statistical Analysis

Normally distributed variables were given as means±SD, whereas non-normally distributed variables were log transformed and given as medians (range). Comparisons between groups were performed by an unpaired Student's t-test or ANOVA. A chi-square was used to compare non-continuous variables. Analyses of the relation at baseline between NT-proBNP and presence/absence of nephropathy or major cardiovascular disease were adjusted for sex, age, systolic blood pressure, and glomerular filtration rate. A two-tailed p-value≦0.05 was considered statistically significant.

All time-to-death variables were analyzed with log rank test and displayed on Kaplan-Meier plots according to presence of nephropathy or NT-proBNP levels above or below the median value. In patients with nephropathy, covariate-adjusted Cox's regression models were fitted with the following pre-specified baseline covariates: sex, age, glomerular filtration rate, smoking, history of major cardiovascular disease, ongoing antihypertensive medication at time of blood sampling, and loglo NT-proBNP or NT-proBNP above respective below the median value (110 ng/l). Further adjustments were not performed to avoid over-fitting of the model. Results are described as hazard ratios with 95% confidence intervals without or with adjustment for other factors that might affect prognosis.

All calculations were performed with a commercially available program (SPSS for WINDOWS, version 10.0).

Results

Type 1 diabetic patients with and without diabetic nephropathy were closely matched with respect to sex, age, and duration of diabetes. As compared with patients with normoalbuminuria, patients with diabetic nephropathy had elevated blood pressure, raised $HbA_{1c}$, increased serum cholesterol, and a lower glomerular filtration rate, p<0.0001. On average, glomerular filtration rate was well preserved in patients with diabetic nephropathy (Table 3).

concentrations were higher in patients taking antihypertensive medication at the time of sampling. This difference, however, disappeared after adjustment for glomerular filtration rate.

A weak inverse correlation between estimated glomerular filtration rate (median 92 ml/min/1.73 m² (range: 45-170)) and plasma NT-proBNP (r=−0.22, p=0.002) was demonstrated in patients with normoalbuminuria.

The prevalence of major cardiovascular events differed between patients with and without diabetic nephropathy, 11% (95% CI: 8-14) and 2% (0-4) respectively, p<0.0001. In patients with nephropathy, plasma NT-proBNP at baseline was significantly elevated in patients with a history of either non-fatal myocardial infarction and/or stroke (671 (34-12418) ng/l, p<0.0001) as compared with those patients without a history of major cardiovascular disease (97 (5-79640) ng/l). After adjusting for possible confounders, a ten-fold increase in NT-proBNP conferred an increase in odds ratio of a major cardiovascular event of 3.1 (95% CI 1.2-7.8), p=0.02.

During follow-up, 51 (26%) patients with and 11 (6%) patients without nephropathy died, p<0.0001. Due to the low

TABLE 3

Baseline clinical and laboratory characteristics
of 386 Type 1 diabetic patients with and without diabetic nephropathy

|  | Nephropathy n = 198 | Normoalbuminuria n = 188 | P-value |
| --- | --- | --- | --- |
| Sex (male/female) | 122/76 | 114/74 | 0.84 |
| Age (years) | 41.0 (9.5) | 42.5 (9.9) | 0.14 |
| Duration of diabetes (years) | 27.7 (8.0) | 26.8 (8.5) | 0.26 |
| Retinopathy (nil/simplex/proliferative) | 0/137/61 | 66/103/19 | <0.001 |
| History of MI | 10 (5.1%) | 2 (1.1%) | 0.036 |
| History of stroke | 14 (7.1%) | 1 (0.5%) | 0.001 |
| BMI (kg/m2) | 24.0 (3.3) | 23.7 (2.5) | 0.20 |
| HbA1c (%) | 9.6 (1.5) | 8.5 (1.1) | <0.001 |
| Urinary albumin excretion (mg/24 h) | 794 (16-14 545) | 8 (1-30) | — |
| S-creatinine (μmol/l) | 103 (54-684) | 76 (40-116) | <0.001 |
| GFR (ml/min) | 74 (33) | 94 (16) | <0.001 |
| Systolic blood pressure (mmHg) | 151 (23) | 132 (18) | <0.001 |
| Diastolic blood pressure (mmHg) | 86 (13) | 76 (10) | <0.001 |
| Antihypertensive drugs at sampling (%) | 34% | 4% | <0.001 |
| S-cholesterol (mmol/l) | 5.6 (1.2) | 4.8 (1.0) | <0.001 |
| S-HDL-cholesterol (mmol/l) | 1.46 (0.54) | 1.56 (0.53) | 0.07 |
| S-triglycerides (mmol/l) | 1.22 (0.30-9.90) | 0.77 (0.30-3.10) | <0.001 |
| Smokers (%) | 50% | 43% | 0.17 |

Data are n, means (SD), medians (range). Some patients with previously persistent albuminuria receiving antihypertensive medication had a urinary albumin excretion rate<300 mg/24 h.

In patients with diabetic nephropathy, plasma NT-proBNP concentration was elevated 110 (5-79640) ng/l (median (range)) versus 27 (5-455) ng/l in normoalbuminuric patients, p<0.0001. This difference persisted after adjustment for differences in glomerular filtration rate and other covariates, p<0.0001. NT-proBNP concentration was elevated early in diabetic nephropathy (40 (5-3111) ng/l), when glomerular filtration rate was still within the normal range (>100 ml/min).

In the nephropathy group, plasma concentration of NT-proBNP did not differ significantly between Type 1 diabetic men and women (p=0.28), but increased with age (r=0.42, p<0.0001), systolic blood pressure (r=0.53, p<0.0001), and decreased with glomerular filtration rate (r=−0.60, p<0.0001) and hemoglobin (r=−0.52, p<0.0001). No correlations between NT-proBNP and either blood glucose, $HbA_{1c}$ or serum cholesterol were observed. No association between diabetic retinopathy and NT-proBNP was found. Among patients with diabetic nephropathy, circulating NT-proBNP numbers of events in the normoalbuminuric group, further analyses are restricted to patients with nephropathy. Within the nephropathy group, the median value of plasma NT-proBNP was 110 ng/l, and 39 (39%) of patients with values above and 12 (12%) of patients with values below this value died from any cause. The unadjusted hazard ratio was 3.86 (95% CI 2.02-7.37), p<0.0001; covariate adjusted hazard ratio 2.28 (1.04-4.99), p=0.04—FIG. 4. This lower mortality was attributable to fewer cardiovascular deaths: 31 (31%) and 7 (7%) above and below the median NT-proBNP level respectively (unadjusted hazard ratio 5.25 (2.31-11.92), p<0.0001; covariate adjusted 3.81 (1.46-9.94), p=0.006—FIG. 5). The effect of plasma NT-proBNP on all cause and cardiovascular mortality remained significant after adjustment for differences in glomerular filtration rate. Furthermore, the interaction between NT-proBNP and glomerular filtration rate was not significant, thus indicating that the effect of NT-proBNP concentration on mortality and cardiovascular mortality is not dependent on the level of glomerular filtration rate. Further adjustment for serum cholesterol and systolic blood pressure did not alter hazard ratios substantially, and results remained significant.

The overall (log rank test, p=0.06) and cardiovascular (p=0.07) mortality in patients with nephropathy and a plasma NT-proBNP level below 110 ng/l were not statistically different from the normoalbuminuric group (FIGS. 2 and 3).

By applying the cutoff of 125 ng/l NT-proBNP recommended in the USA, covariate adjusted hazard ratios for all cause and cardiovascular mortality were only slightly changed: 2.68 (1.24-5.79), p=0.01 and 4.09 (1.61-10.41), p=0.003 respectively.

Cox regression analyses including NT-proBNP concentration as continuous variable revealed an unadjusted hazard ratio for all cause mortality for each 10-fold increase in NT-proBNP of 3.39 (2.38-4.82), p<0.0001; covariate adjusted 2.67 (1.62-4.42), p<0.0001. Accordingly for cardiovascular mortal the unadjusted hazard ratio for each 10-fold increase in NT-proBNP was 3.58 (2.40-5.36), p<0.0001; covariate adjusted 3.32 (1.90-5.81), p<0.0001.

In conclusion, elevated circulating NT-proBNP is an independent predictor of the excess overall and cardiovascular mortality in diabetic nephropathy. The measurement of NT-proBNP adds prognostic information to available methods and can help to guide management of Type 1 diabetic patients with diabetic nephropathy.

Example 3

Figure 6:
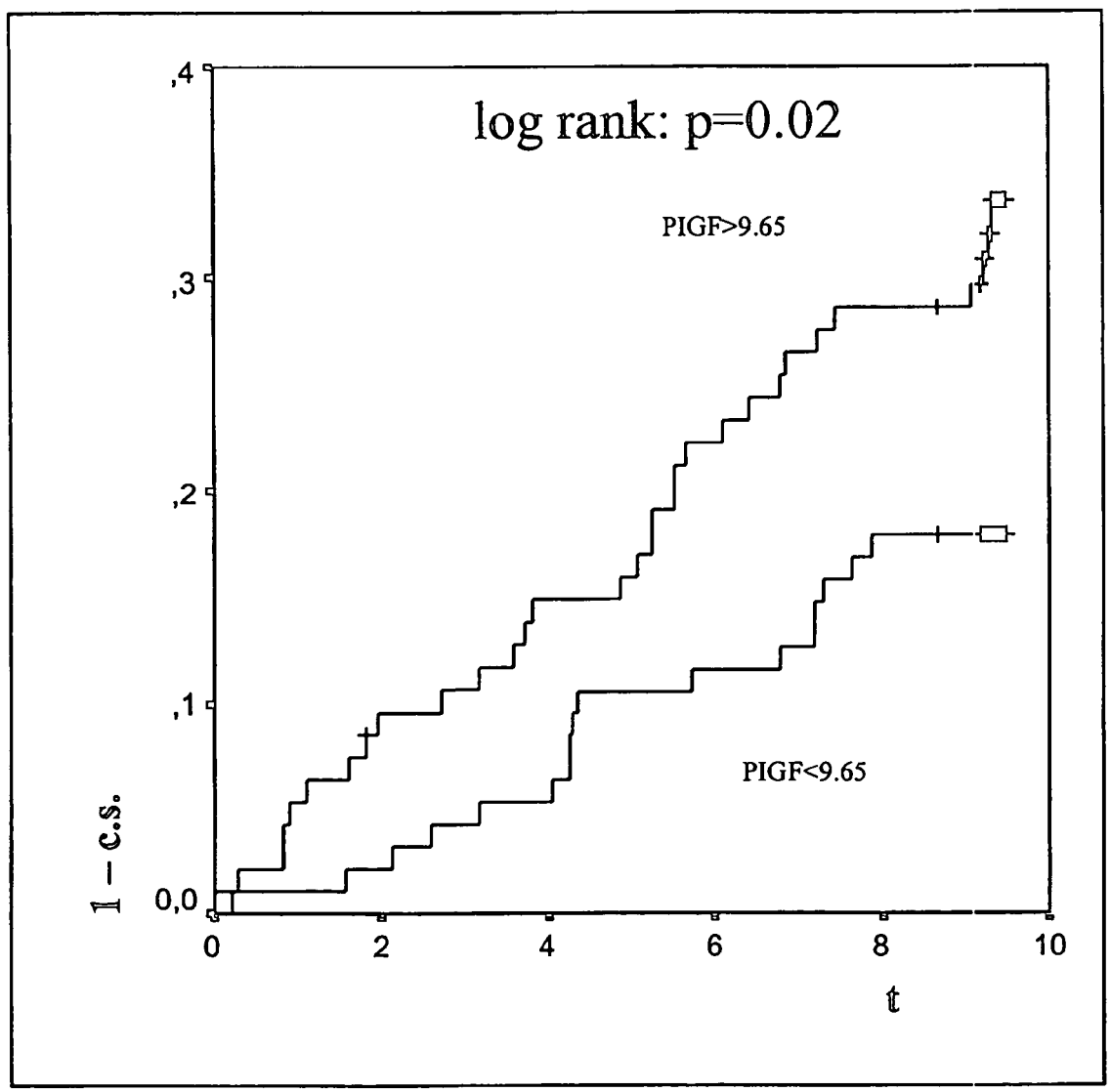
FIG. 6 shows a Kaplan-Meier plot depicting all cause mortality in Type 1 diabetic nephropathy according to plasma PlGF. The data Was collected during the Steno-1 study as described in Example 2. 1–c.s., one minus cumulative survival; t, follow-up time (years).
Figure 7:
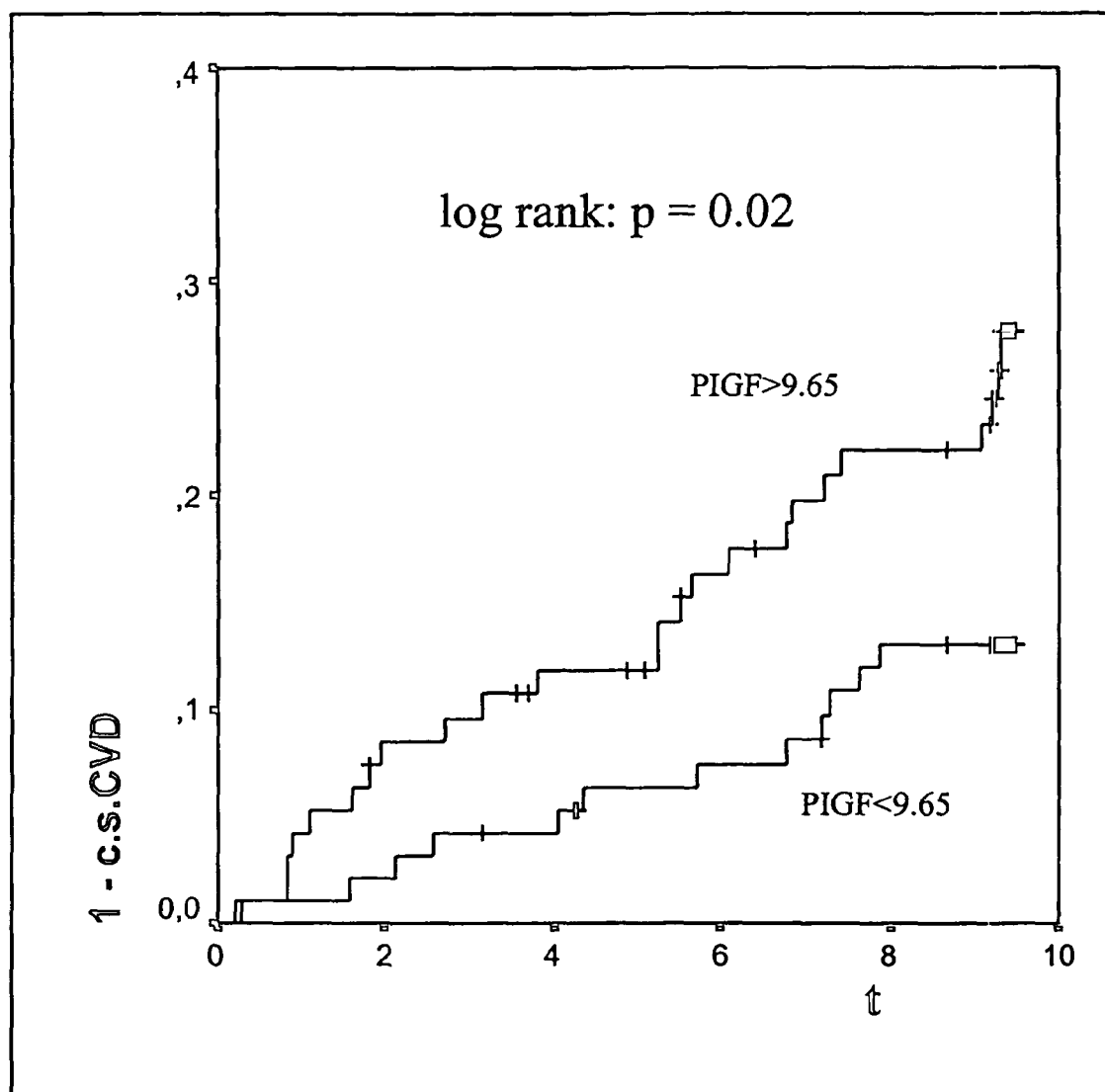
FIG. 7 shows a Kaplan-Meier plot depicting mortality from cardiovascular disease in Type 1 diabetic nephropathy according to plasma PlGF. The data was collected during the Steno-1 study as described in Example2. 1–c.s. CVD, one minus cumulative survival from mortality by cardiovascular disease; t, follow-up time (years).

In diabetes Type 1 patients with nephropathy; PlGF was found not to be correlated with age, sex, HbA1c, and, glomerular filtration rate. Correlation with urinary albumin excretion was weak. In diabetes Type 1 patients with nephropathy, PlGF was correlated with mortality from any cause and mortality from cardiovascular disease (FIGS. 6 and 7).

Example 4

Table 4 shows an analysis of PlGF in patients of the Steno-2 study. The general study design has been described in Example 1.

TABLE 4

Cardiovascular disease and plasma PlGF

|  | Plasma as baseline predictor for any CVD event (continuous) | Plasma PlGF as baseline predictor for any CVD event (below/above median) |
| --- | --- | --- |
| Entire Steno-2 cohort | Hazard ratio 1.073 (0.999 to 1.152), p = 0.052 | Hazard ratio 1.22 (0.71 to 2.08), p = 0.48 |
| Intensive therapy group | Hazard ratio 1.21 (1.04 to 1.41), p = 0.012 | Hazard ratio 2.19 (0.79 to 6.08), p = 0.13 |
| Standard therapy group | Hazard ratio 1.03 (0.95 to 1.12), p = 0.46 | Hazard ratio 1.04 (0.53 to 2.04), p = 0.91 |

Example 5

A 55-year old diabetes Type 2 patient presents at his general practitioner. NT-proBNP (357pg/ml), PlGF (11 pg/ml) and free non-thrombocyte-bound) sCD40L. (1.2 pg/ml) are measured. The patient does not complain of chest pain. The NT-proBNP value indicates the presence of heart disease. The patient is referred to a cardiologist for thorough cardiac examination. ECG and cardiac troponin T are normal. The dose of rosiglitazone medication is reduced, and treatment with ACE inhibitors and diuretics is initiated. In the following, NT-proBNP is monitored at bi-weekly intervals and reaches a level of 117 pg/ml after two months. Additionally, the level of cardiac troponin T is monitored regularly.

Example 6

A 62-year old female diabetes Type 2 patient presents at her diabetes specialist. NT-proBNP (37 pg/ml), PlGF (27 pg/ml) and free sCD40L (1.0 pg/ml) are measured. NT-proBNP and PlGF indicate a presence or risk of cardiovascular complication with a predominant characteristic of microangiopathy. VEGF is measured and confirms the diagnosis. CML and HbA1c (7.7%) are measured and indicate insufficient control of blood sugar. The patient is advised to seek regular exercise and to inspect her extremities daily for small injuries or signs of hypoxia. Medication with statins and glitazones is initiated. NT-proBNP is measured at short intervals to detect whether treatment with glitazones causes an increase in the risk of heart disease. PlGF, AGE, CML, and HbA1c are measured monthly to monitor the success of treatment.

What is claimed is:

1. A method for diagnosing a cardiovascular complication or a risk of a cardiovascular complication in a diabetes patient who is clinically asymptomatic for cardiac disease, the method comprising the steps of:
    measuring in vitro the level of placental growth factor-1 (PlGF-1) in a sample from the patient,
    measuring in vitro the level of at least one additional marker for a cardiovascular complication or a risk of a cardiovascular complication, wherein the additional marker is selected from the group consisting of N-terminal pro brain natriuretic peptide (NT-proBNP), C-reactive protein (CRP), high-sensitivity C-reactive protein (hsCRP), and interleukin 6 (IL-6), and
    diagnosing the cardiovascular complication or the risk of a cardiovascular complication by comparing the measured levels to known levels associated with the cardiovascular complication or the risk, wherein a measured level of PlGF-1 higher than the known level associated with cardiovascular complication or risk, and a measured level of at least one or more of NT-proBNP, CRP, hsCRP, and IL-6 higher than the known level associated with cardiovascular complication, is indicative of a diagnosis of the cardiac complication or risk.

2. The method of claim 1 wherein the patient is suffering from Type 2 diabetes.

3. The method of claim 1 wherein the patient is suffering from diabetic nephropathy.

4. The method of claim 1 further comprising the step of diagnosing a manifestation of diabetes selected from the group consisting of inflammation and insufficient control of blood sugar level,
    wherein a diagnosis of inflammation is made by measuring in vitro a level of CRP, hsCRP or IL-6 in a sample from a patient and comparing the measured level to a known level of CRP, hsCRP or IL-6 associated with inflammation, wherein a measured level higher than the known level is indicative of a diagnosis of inflammation; and
    wherein a diagnosis of insufficient control of blood sugar level is made by measuring in vitro a level of glucose, hemoglobin A1c (HbA1c), $N^{\epsilon}$-(carboxymethyl)lysine (CML) or advanced glycation endproducts (AGEs) in a sample from a patient and comparing the measured level to a known level of glucose, HbA1c, CML or AGEs associated with insufficient control of blood sugar level, wherein a measured level higher than the known level is indicative of a diagnosis of insufficient control of blood sugar level.

* * * * *